United States Patent [19]
Silberstein

[11] Patent Number: 4,869,264
[45] Date of Patent: Sep. 26, 1989

[54] ELECTROENCEPHALOGRAPHIC CONSCIOUSNESS AND ANESTHETIC MONITOR

[75] Inventor: Richard B. Silberstein, Blackburn, Australia

[73] Assignee: Swineburn Limited, Victoria, Australia

[21] Appl. No.: 49,694

[22] PCT Filed: Jul. 28, 1986

[86] PCT No.: PCT/AU86/00214
§ 371 Date: Mar. 30, 1987
§ 102(e) Date: Mar. 30, 1987

[87] PCT Pub. No.: WO87/00745
PCT Pub. Date: Feb. 12, 1987

[30] Foreign Application Priority Data

Jul. 30, 1985 [AU] Australia ............. PH01701/85

[51] Int. Cl.⁴ .................................. A61B 5/04
[52] U.S. Cl. ........................ 128/731; 128/741; 128/745
[58] Field of Search ........... 128/731, 732, 1 C, 741, 128/745

[56] References Cited

U.S. PATENT DOCUMENTS

| | | | |
|---|---|---|---|
| 3,087,487 | 4/1963 | Clynes | 128/731 |
| 3,513,834 | 5/1970 | Suzuki et al. | 128/731 |
| 3,689,135 | 9/1972 | Young et al. | 351/39 |
| 4,201,224 | 5/1980 | John | 128/731 |
| 4,570,640 | 2/1986 | Barsa | 128/741 |

OTHER PUBLICATIONS

"Proceedings of the Eleventh Annual Northeast Bioengineering Conference", 14th–15th Mar. 1985, Worcester, MA, pp. 128–134, IEEE, NY, US; J. H. Strickland, Jr., et al.: Visual Evoked Response Phase Spectrum as Measure of Latency.

"Measuring the Level of Anesthesia by Automatic Analysis of Spontaneous EEG Activity", McEwen et al., IEEE Transactions on Biomedical Engineering, Jul. 1975, pp. 299–305.

Primary Examiner—William E. Wayner
Attorney, Agent, or Firm—Wolf, Greenfield & Sacks

[57] ABSTRACT

A method and apparatus for testing the anesthetic depth or consciousness of a subject by directing visible red stimulus signals at the eyes of the subject through closed eyelids at accurately known frequencies. An electroencephalographic (EEG) signal is then obtained and a discriminator (18) is used to accurately detect components at the applied frequencies. An assessment is then made by comparing the magnitude or phase of the components of the EEG signal at the predetermined frequencies with correspondingly obtained EEG signals which have been obtained prior to administration of anesthetic to the subject.

27 Claims, 13 Drawing Sheets

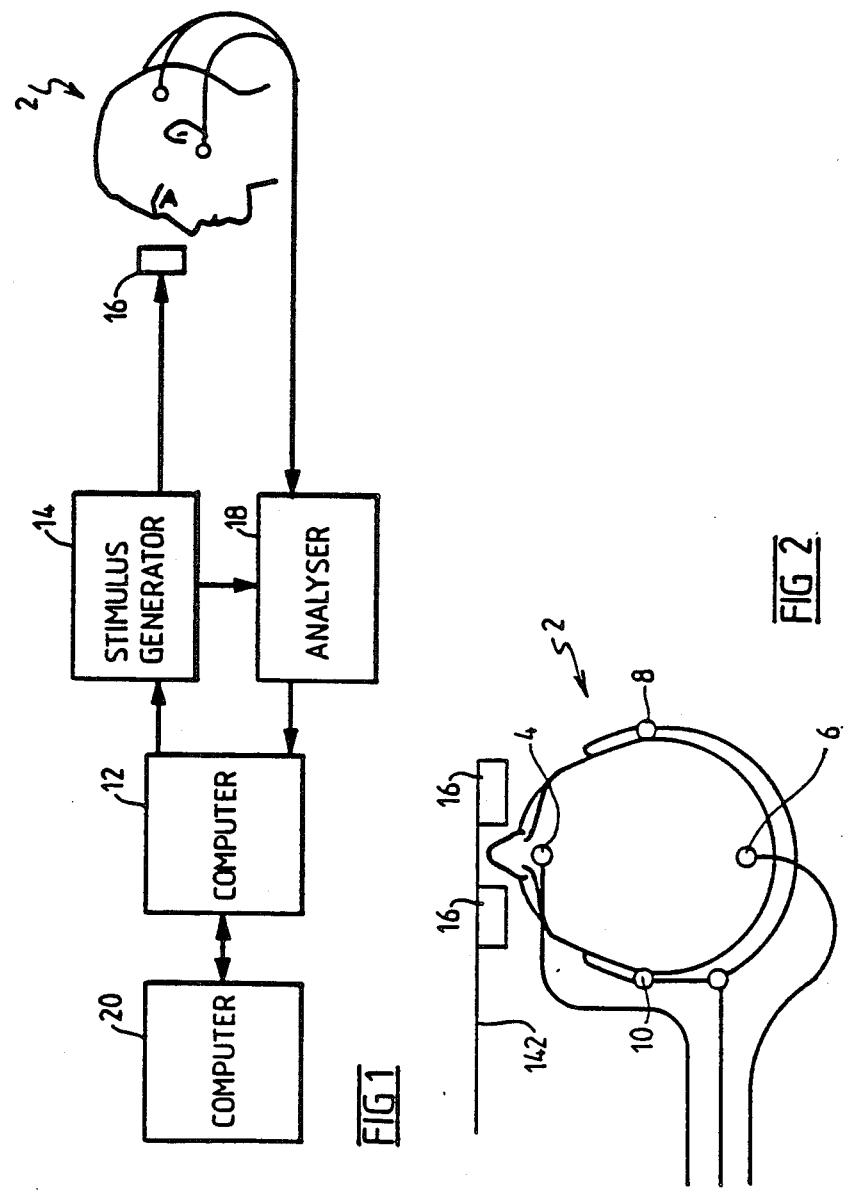

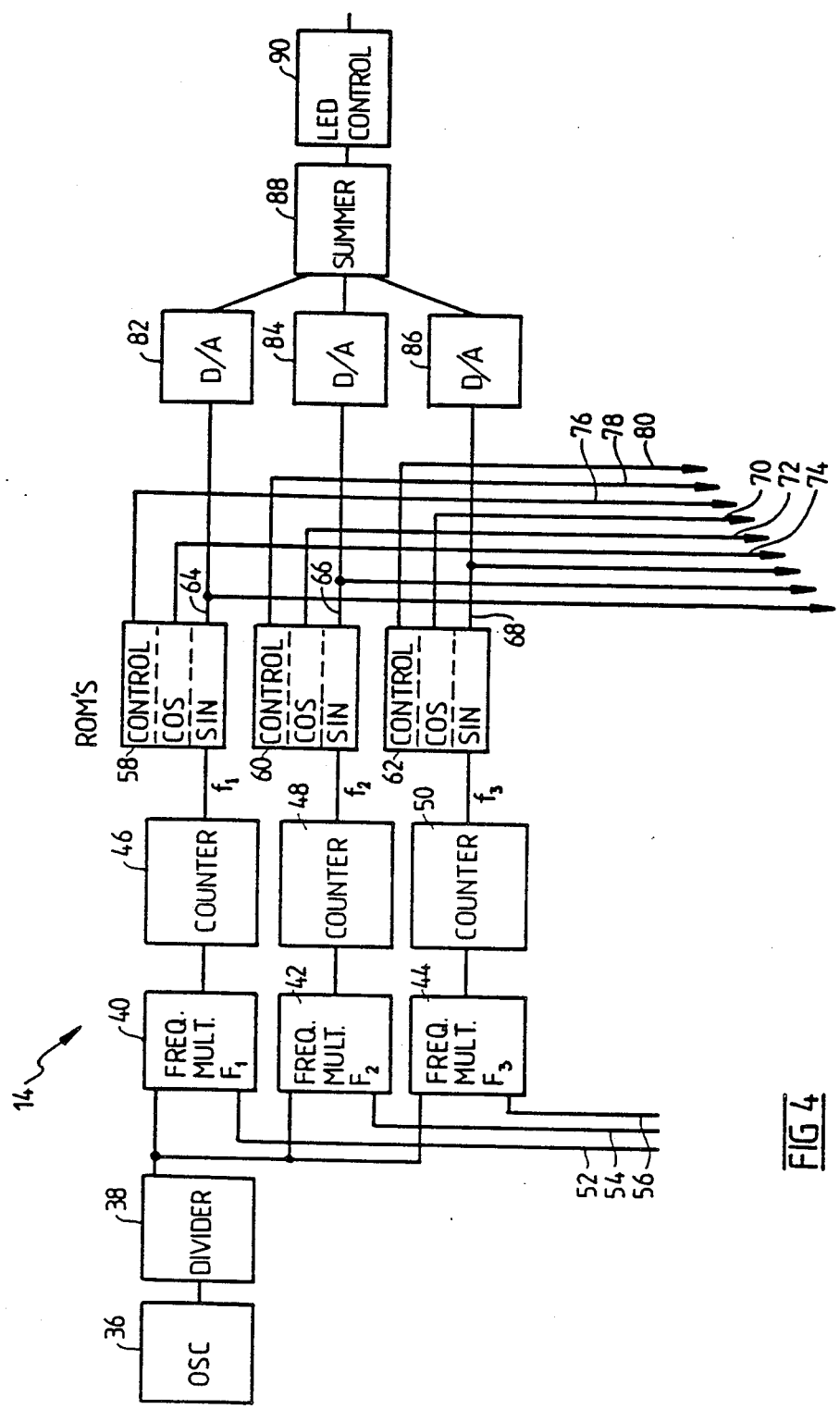

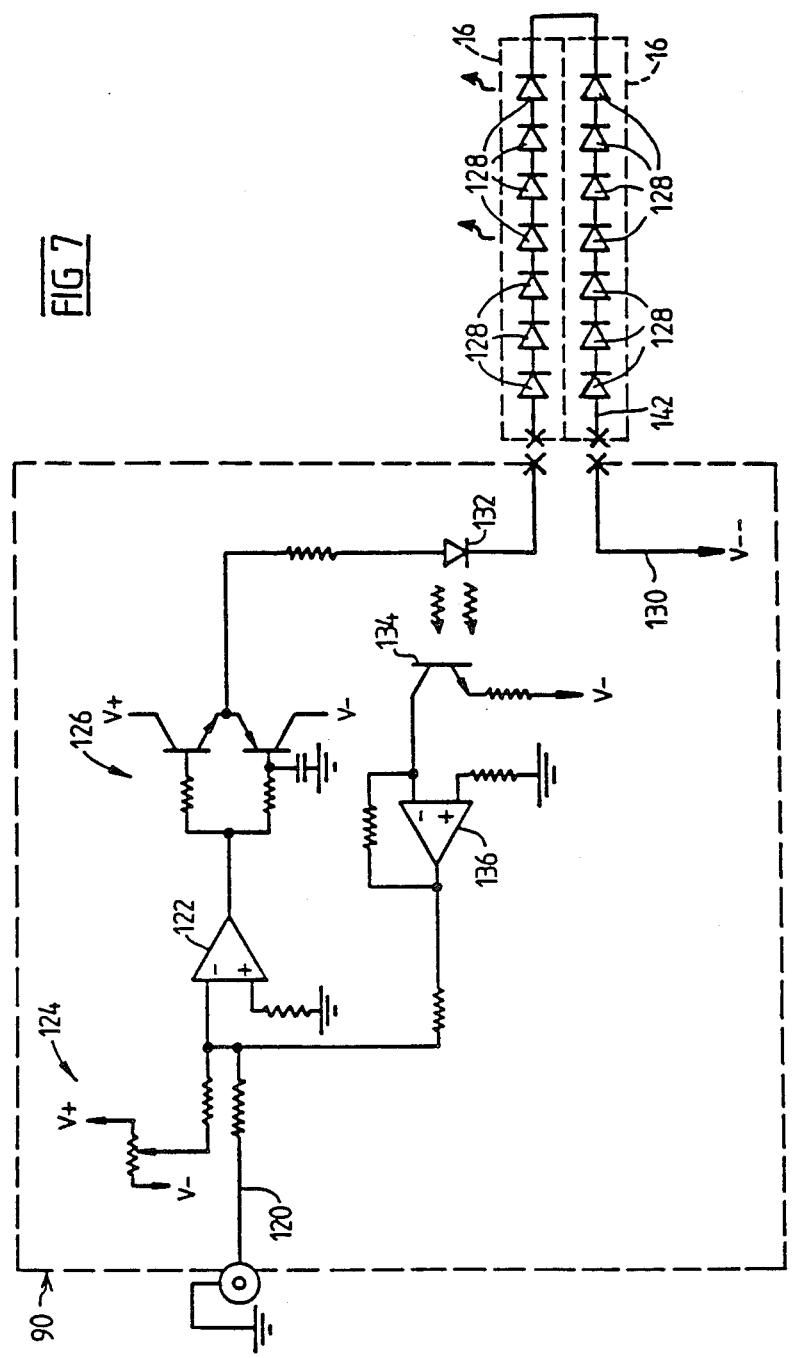

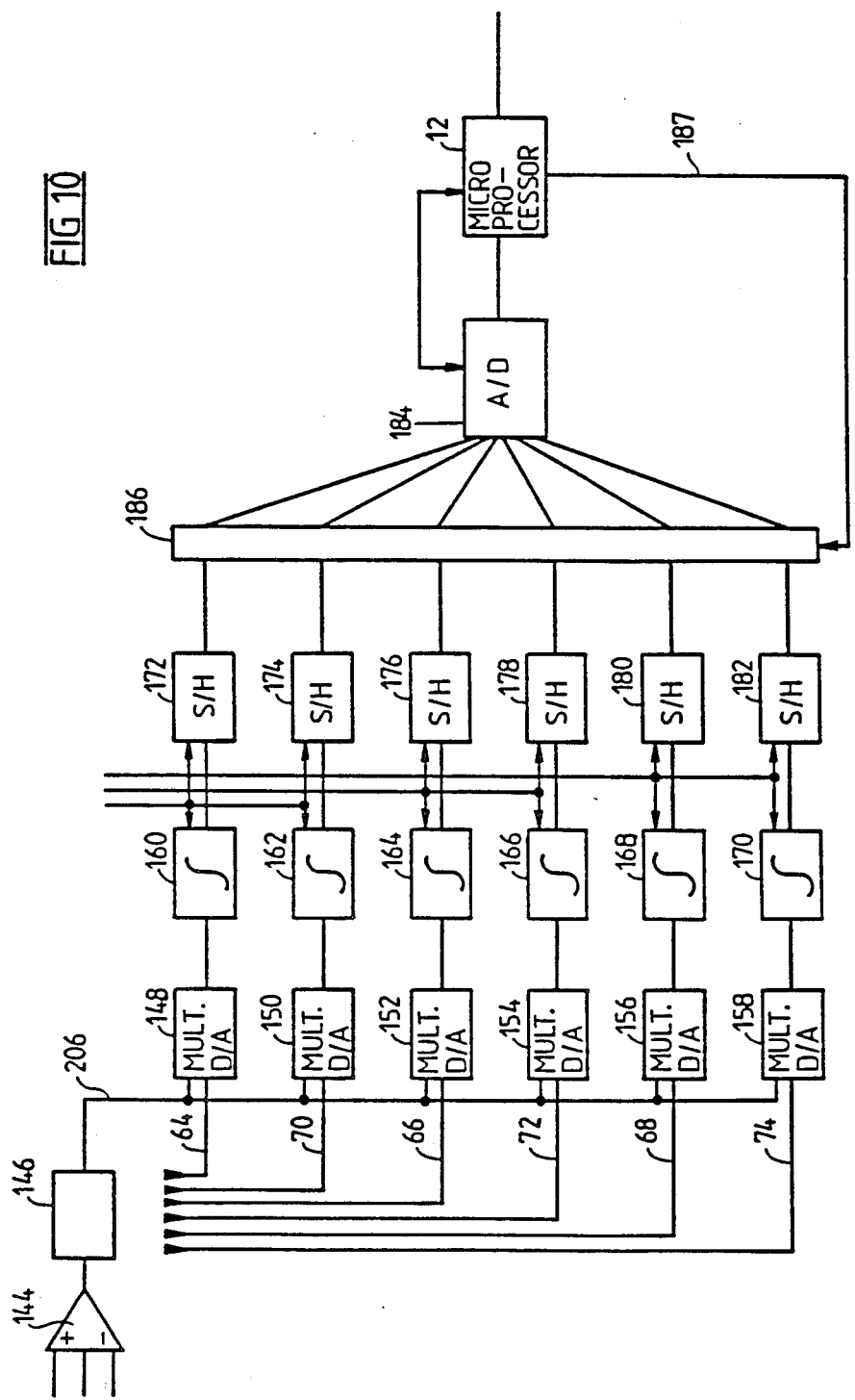

ELECTROENCEPHALOGRAPHIC CONSCIOUSNESS AND ANESTHETIC MONITOR

This invention relates to an anaesthetic monitor.

More particularly the invention relates to a method and apparatus for monitoring the level of consciousness of a subject who has been subjected to a general anaesthetic. Information concerning anaesthetic depth and the level of consciousness would be of considerable usefulness to the person administering the anaesthetic so that the administration of the anaesthetic can be controlled so as to give a desired anaesthetic depth and level of consciousness.

According to the present invention there is provided a method of testing anaesthetic depth or consciousness of a subject comprising the steps of applying a stimulus signal including at least one component of a predetermined frequency to a sensory organ of the subject, obtaining an electroencephalographic (EEG) signal from the subject whilst said stimulus signal is being applied, analysing the EEG signal so as to determine the magnitude and/or phase of that component of the EEG signal which has said predetermined frequency, and assessing the anaesthetic depth or consciousness of the subject with reference to said magnitude and/or phase of the component.

Preferably, the method includes steps for applying a stimulus signal having a plurality of predetermined frequency components therein and the analysis of the EEG signal is carried out to determine the magnitude and/or phase of the respective components in the EEG having the same frequencies as the stimulus signal.

Preferably further, the method includes the step of simultaneously applying selected groups of said frequency components.

Preferably further, the stimulus signal comprises electromagnetic radiation. Preferably further, the radiation comprises visible red radiation modulated in amplitude so as to have components at said plurality of predetermined frequencies. Preferably further, the frequency components are in the range of 4 to 72 Hz. The method may be used to test the consciousness of a subject under anaesthetic and, in this application, the method includes the step of administering anaesthetic in accordance with the magnitude and/or phase of the components.

In this case, the preferred method of treating the subject is to subject the subject to the method prior to administration of the anaesthetic so as to determine a pre-anaesthetic magnitude and/or phase response of the selected component of the EEG signal (hereinafter called a normal response). The anaesthetic is then administered and the method includes the step of comparing the magnitude after administration of the anaesthetic to the normal response. The comparisons are preferably carried out and displayed as a function of frequency of the stimulus signal.

The invention also provides apparatus for testing consciousness of a subject, said apparatus comprising generator means for generating a stimulus signal having at least one component of a predetermined frequency, coupling means for coupling the stimulus signal to a sensory organ of the subject, EEG electrodes for deriving an EEG signal from the subject and discriminating means for obtaining the magnitude and/or phase of that component of the EEG signal which has said predetermined frequency.

Where the apparatus is to be used for testing the consciousness of a subject under anaesthetic, it is important that the apparatus yields the information quickly regarding the magnitude and/or phase of the selected frequency component of the EEG signal so that personnel administering the anaesthetic will be in a position to monitor the results and thereby control the rate of administration of the anaesthetic to the subject.

The invention will now be further described with reference to the accompanying drawings, in which:

FIG. 1 is a block diagram showing the basic components of the anaesthetic monitoring system of the invention;

FIG. 2 is a schematic plan view showing EEG electrodes and Light Emitting Diode (LED) arrays relative to a subject;

FIG. 4 is a block diagram showing the stimulus generator;

FIG. 7 is a circuit for controlling the intensity of an LED array;

FIG. 10 is a block diagram showing the EEF analyser;

Figure 3A:
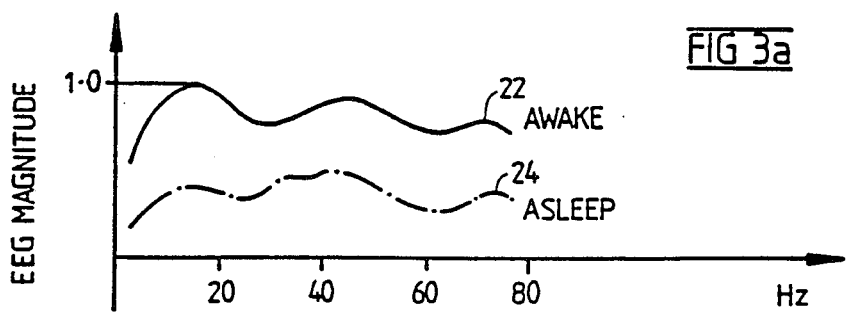
FIGS. 3A to 3D illustrate graphical output displays of the system.

The system schematically illustrated in FIG. 1 is used for determining the state of awareness or anaesthetic depth of a subject 2 who might for instance be undergoing a surgical operation. An EEG signal from the subject is obtained by using EEG electrodes 4, 6, 8 and 10.

FIG. 2 shows one way in which the electrodes are coupled to the head of the subject 2. In this arrangement the electrode 4 is coupled to the forehead of the subject and is used as a ground. The electrode 6 is coupled at the central occipital site (Oz) and the electrodes 8 and 10 are connected to the ears of the subject. The electrodes 8 and 10 and electrically connected together and form the negative input for the analyser, as will be described hereinafter.

The system includes a microcomputer 12 coupled to a stimulus generator 14 which in turn is coupled to a pair of LED arrays 16. The LED arrays are in use located adjacent to the eyes of the subject 2 and are arranged to generate signals which are perceptible through the closed eyelids of the subject. The system includes an analyser 18 which analysers the EEG signals obtained from the electrodes 4, 6, 8 and 10. Output from the analyser is coupled to the microcomputer 12. The computer 12 arranges for further processing of the output of the analyser in a general purpose computer 20 which may include a VDU display for display of results in numerical or graphical form.

Generally speaking, the stimulus generator generates a stimulus signal which comprises one or a group of accurately known frequency components. The stimulus signal is applied to the pair of LED arrays so as to modulate the intensity thereof. The electrical response of the brain of the subject is sensed using the EEG electrodes and the analyser 18 very accurately isolates the components which have the same frequency or frequencies as the stimulus signal produced by the stimulus generator 14. It has been found that this technique enables very useful information to be obtained regarding the anaesthetic depth of a subject. It has also been found that certain frequencies are especially useful in ascertaining the anaesthetic depth of the subject but the peak sensitivity of some subjects occurs at different frequencies. Accordingly, the preferred technique of the invention involves applying signals to the subject at a range of frequencies. In order to conserve time, a group of say three selected frequencies are applied simultaneously to the subject and the analyser 18, microcomputer 12 and computer 20 are arranged to separately analyse the response to the individual frequencies in the selected group. Table 1 below sets out a typical selection of frequencies.

TABLE 1

| GROUP | $F_1$(Hz) | $F_2$(Hz) | $F_3$(Hz) | Duration | Typical Sensitivity |
|---|---|---|---|---|---|
| 1 | 4 | 5 | 6 | 20 sec | reasonable |
| 2 | 7 | 8 | 9 | 20 sec | reasonable |
| 3 | 10 | 11 | 12 | 40 sec | not very selective |
| 4 | 13 | 14 | 15 | 20 sec | not very selective |
| 5 | 16 | 17 | 18 | 10 sec | satisfactory |
| 6 | 20 | 22 | 24 | 10 sec | satisfactory |
| 7 | 26 | 28 | 30 | 10 sec | satisfactory |
| 8 | 32 | 34 | 36 | 10 sec | satisfactory |
| 9 | 38 | 40 | 42 | 10 sec | best |
| 10 | 44 | 46 | 48 | 10 sec | best |
| 11 | 50 | 52 | 54 | 10 sec | best |
| 12 | 56 | 58 | 60 | 10 sec | best |
| 13 | 62 | 64 | 66 | 10 sec | best |
| 14 | 68 | 70 | 72 | 10 sec | best |

The table indicates that there are fourteen groups of frequencies $F_1$, $F_2$ and $F_3$, the duration for which the group of frequencies is applied and the typical sensitivity of a subject to those particular frequencies. The duration is chosen so that a reasonably accurate EEG response can be obtained, e.g. a signal to noise ratio of 3 dB in a relatively short period. In the period were too long, the system would not yield results quickly enough for monitoring the anaesthetic depth of a subject under an anaesthetic. The selection of frequencies within the groups is arbitrary but for convenience the frequencies $F_1$, $F_2$ and $F_3$ are adjacent so that the optimum durations are also similar. It has been found that for signals above about 72 Hz the EEG response is too small.

In carrying out the invention, the subject is first subjected to signals from the stimulus generator 14 before any anaesthetic is administered so as to obtain an "awake" response because the EEG amplitudes of subjects vary quite considerably from one to another. The awake response is stored in the general purpose computer 20 so that normalized results can be displayed when the subject is subjected to the stimulus under anaesthetic.

FIG. 3A illustrates the typical EEG magnitude response of a subject as a function of frequency. The solid line 22 shows the "awake" response which is obtained before any anaesthetic is administered, the red light signals being applied through the closed eyelids of the subject as mentioned previously. The graph also shows the "asleep" response 24 as a function of frequency after a subject has been subjected to the anaesthetic. The general purpose computer 20 can be programmed to display a graph in a similar format to that shown in FIG. 3A, the asleep response 24 being continually updated by results obtained from the analyser 18 and microcomputer 12. An operator can then make a comparative assessment to see the ratio of the asleep response 24 to the awake response at a particular frequency. Generally speaking, a useful indication is that the subject is soundly anaesthetized is when the asleep response is less than 50% of the awake response.

Figure 3B:
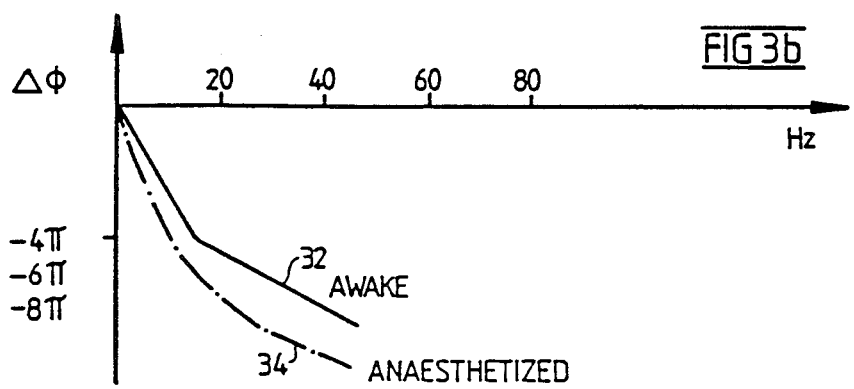
Figure 3C:
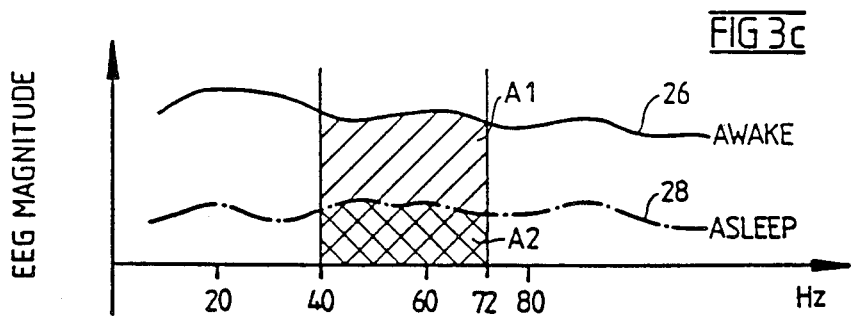
Figure 3D:
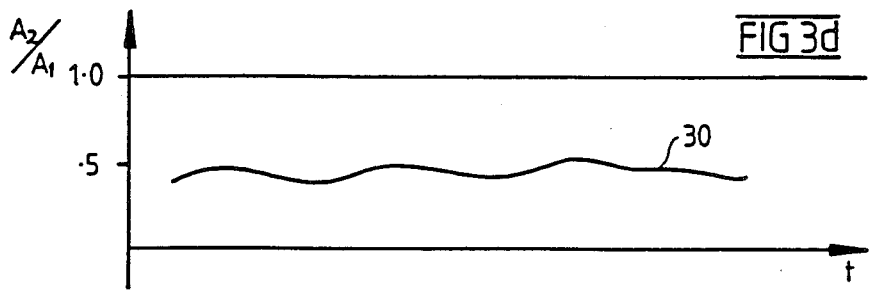

Alternatively, the general purpose computer 20 can be programmed to display the output information as a function of time. FIG. 3C shows the magnitude responses as a function of frequency, the general purpose computer 20 being preprogrammed to integrate to obtain the area $A_1$ beneath the awake response 26 in a selected frequency range say 40 to 72 Hz and to integrate so as to obtain the area $A_2$ beneath the asleep response 28. The ratio response 30 can then be displayed as a function of time as shown in FIG. 3D. Output in this form provides a very convenient indication to an operator of the anaesthetic depth of the subject. Where the ratio response 30 is less than 0.5, that can be taken as an indication that the subject is sufficiently anaesthetized.

It would be possible of course to arrange to automatically control the administration of further anaesthetic into the subject in accordance with the normalized response information available in the computer 20. For safety reasons however it is envisaged that the administration of further anaesthetic would be carried out manually after assessment of the output of the computer by an experienced operator.

In an alternative arrangement, the phase response of the subject could be obtained and utilized in a similar way. For instance, whilst the subject were awake, the phase response of the selected frequency components in the EEG relative to the respective frequency components generated by the stimulus generator could be obtained and stored as a function of frequency. FIG. 3B shows the awake response 32 of the phase difference as a function of frequency. The asleep response 34 is also shown. The phase response is proportional to frequency multiplied by T where T is the delay between input of a stimulus and the EEG response. It has been found that the delay T of a subject varies in accordance with the anaesthetic depth and thereby this parameter can be used for assessment of the anaesthetic depth.

FIGS. 4 to 15 illustrate in more detail a preferred arrangement for the stimulus generator 14, analyser 18 and microcomputer 12.

FIG. 4 shows an oscillator 36 arranged to oscillate at say 4 MHz. The output of the oscillator 36 is coupled to a divider 38 the output of which is coupled to frequency multipliers 40, 42 and 44 the outputs of which are coupled to counters 46, 48 and 50 respectively. The outputs of the counters 46, 48 and 50 comprise square-wave signals, the frequencies of which are accurately determined and comprise the frequency components $F_1$, $F_2$ and $F_3$ to be applied to the subject in accordance with Table 1 above. The actual values of the frequencies produced by the multipliers 40, 42 and 44 are determined in accordance with data input on data lines 52, 54 and 56 from the microcomputer 12. Output from the counters 46, 48 and 50 is applied to ROM's 58, 60 and 62. Each of the ROM's has three functions. First to store a look-up table for sine values and so produce output in digital form on lines 64, 66 and 68, the output being the sine of the number applied to the respective ROM. The ROM's also have cosine look-up tables so as to produce cosine outputs on lines 70, 72 and 74. The ROM's also produce control signals on lines 76, 78 and 80 which are applied to the analyser 18. The sine output lines 64, 66 and 68 are coupled to digital to analogue converters 82, 84 and 86 the outputs of which are summed in an adding circuit 88. The summed output from the summer 88 is applied to an LED control circuit 90 which produces current for the LED arrays 16. Thus, the current signal applied to the LED array 16 has three accurately known frequency components $F_1$, $F_2$ and $F_3$ as determined by the microcomputer 12.

Figure 5:
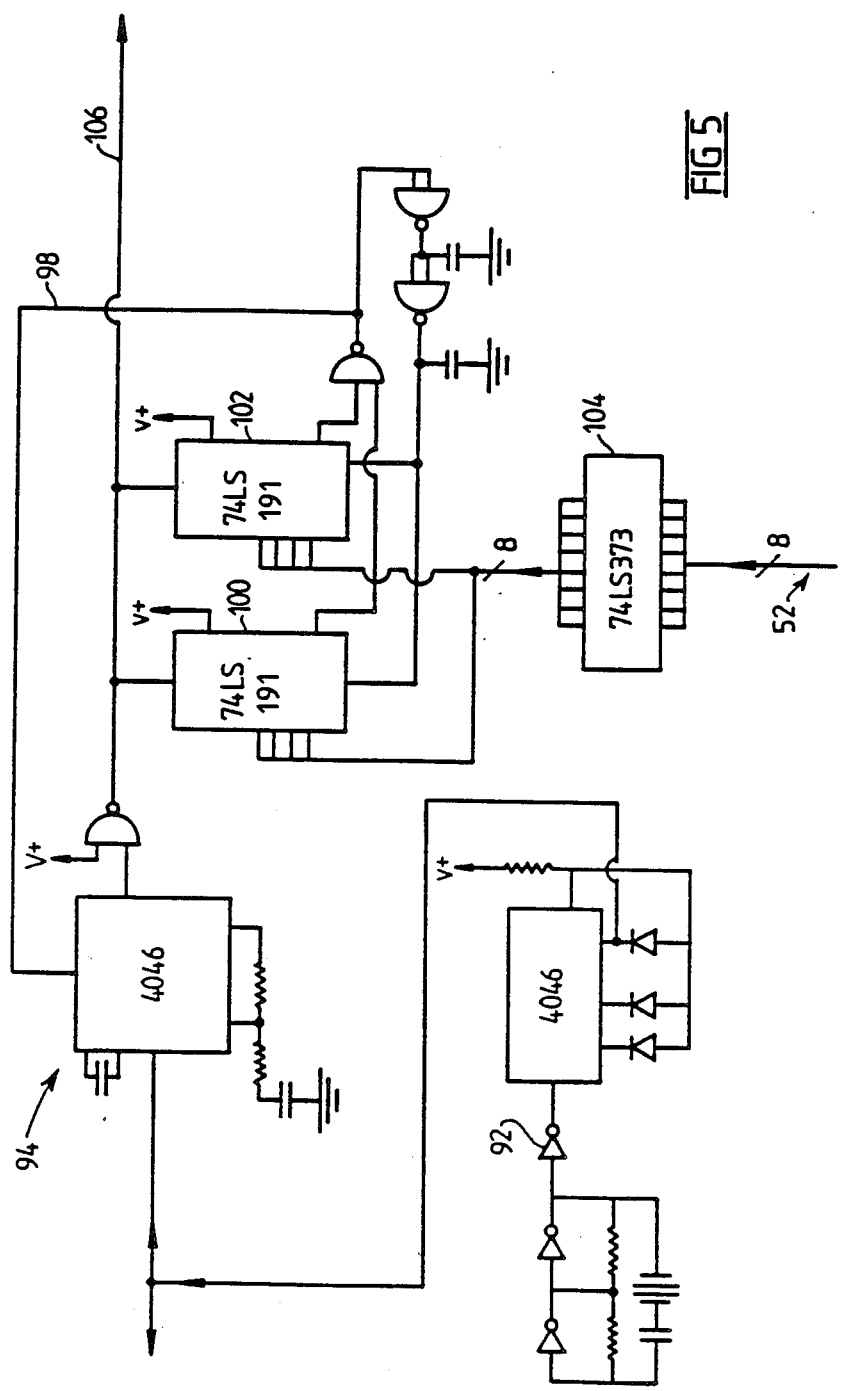
FIG. 5 is a more detailed circuit diagram of part of the stimulus generator.

FIG. 5 shows in schematic form a circuit realization for part of the stimulus generator 14. In this arrangement, the oscillator 36 is a 4 MHz crystal oscillator and its output is coupled to the input of the counter 38 by means of a buffer amplifier 92. The divider 38 conveniently comprises a 4040 counter receiving output from the buffer amplifier 92. The output from the counter comprises a stable accurately defined frequency which for convenience is chosen to be 512 Hz. The output signal is connected to the inputs of the frequency multipliers 40, 42 and 44, the multiplier 40 being shown in more detail in FIG. 6 by way of example. The multiplier 40 comprises a 4046 phase-locked loop circuit 94 which receives output from the counter 38, via pin 14. The circuit includes a divider circuit 96 the output of which is coupled via line 98 to pin 3 of the 4046 circuit. The divider circuit itself includes presettable down counters 100 and 102 each of which comprises a 74 LS 191 circuit. The divider circuit operates to divide by a number read into a 74 LS 373 eight-bit latch 104 from the microcomputer 12 via lines 52. Thus the input to the latch 104 determines the factor by which the divider 96 divides the reference frequency input to the frequency multiplier 40. The output of the multiplier 40 appears on line 106 which is coupled to the input of counter 46. The frequency is 1024 times the frequency $F_1$. The counter 46 comprises a 74 LS 393 counter arranged to divide the input by the factor 1024 whereby its output is at frequency $F_1$.

Figure 6:
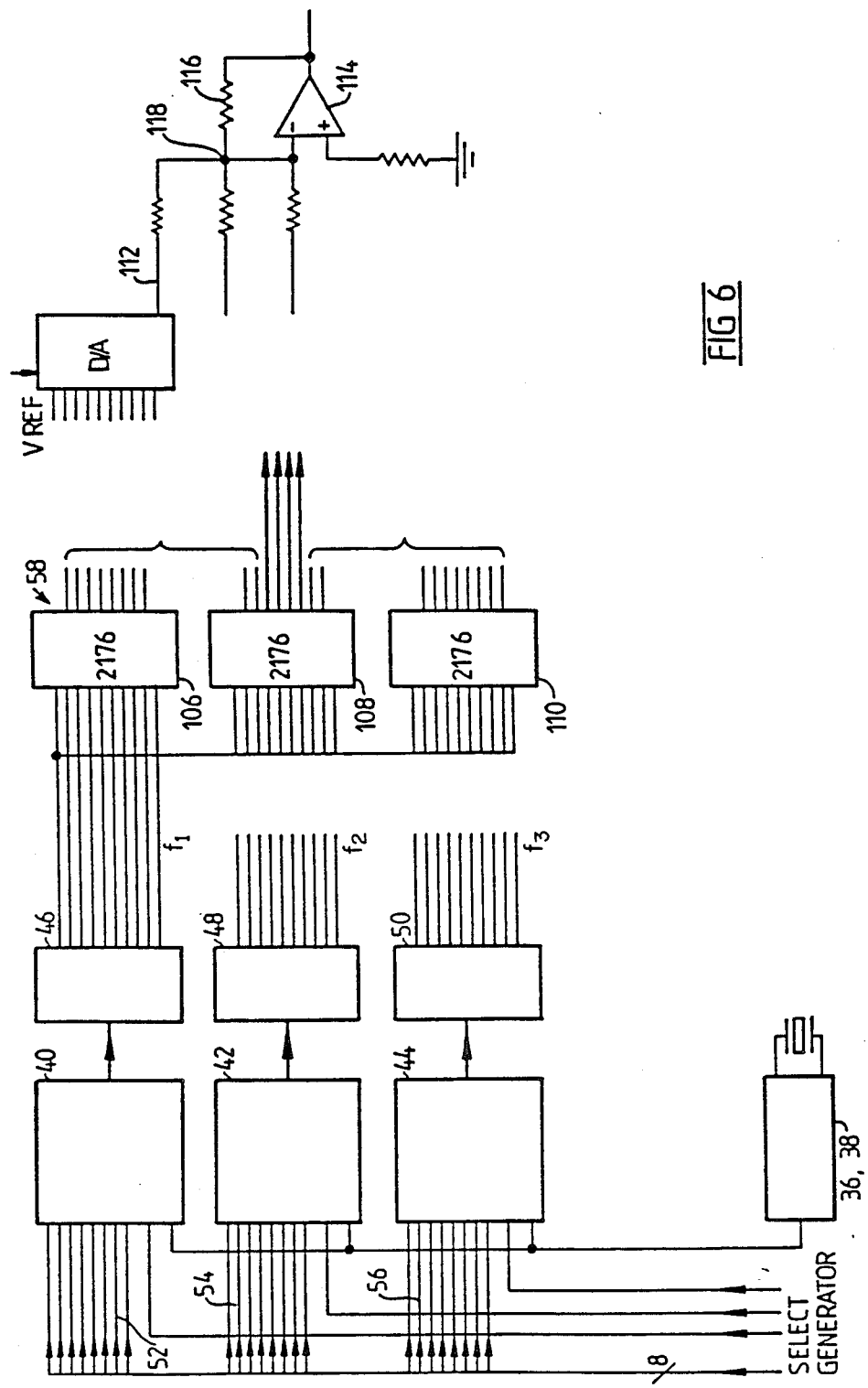
FIG. 6 is another circuit diagram of part of the stimulus generator.

As seen in FIG. 6, the counter 46 has its ten-bit output coupled to the inputs of ROM 58 which preferably comprises three ROM elements 106, 108, 110 each having eight output bits. Eight bits of the element 106 and two from the element 108 are used for the sine output table, and eight bits from the element 110 and two the element 108 are used for the cosine output table. The remaining four bits of the ROM element 108 are connected to the control lines 76 for control signals for the microcomputer 12 and for the analyser 18. The ten-bit sine output from the ROM 58 is then coupled to the input of a digital to analogue converter 82 and the output 112 is connected to one input of the adding circuit 88. The adding circuit comprises a differential amplifier 114 the positive input of which is grounded and the output of which has a resistive feedback element 116 connected to the summing junction 118 which in turn is coupled to the negative input of the amplifier 114. The amplifier 114 may comprise a TL 071 circuit. The other inputs to the adding circuit 88 are derived from the digital to analogue converters 84 and 86 which relate to the reference frequencies $F_2$ and $F_3$ respectively.

Output from the amplifier 114 is coupled to input line 120 of the LED control circuit 90, as shown in FIG. 7. The input line 120 is coupled to the input of an amplifier 122 via a zero adjusting network 124 which is adjusted so that the output of the circuit 90 has a desired DC level. Output from the amplifier 122 is coupled to the input of a current buffer 126 for driving the LED arrays 16. Each array 16 comprises seven LED devices 128 arranged in a circular pattern, as diagrammatically illustrated in FIG. 8. The fourteen LED's are connected in series and are driven by the current supplied from the buffer 126. The other end of the series connection of LED's is connected to a negative supply line 130 the voltage of which is selected to accordance with the number of LED's connected in series. In order to regulate the intensity of the output of the array 16, a control LED 132 is connected in series with the output of buffer 126 and arranged to irradiate a phototransistor 134, the output of which is connected via amplifier 136 to the input of the amplifier 122. The output of the control LED 132 which is selected so as to be of the same type as those used in the array 16 is thus representative of the light intensity output of the array and this is used for negative feedback so as to control the peak intensity reached by the LED arrays 16. The circuit 90 thus ensures a constant average level of intensity of light output from the LED array 16 regardless of which selected group of reference frequencies is applied to the LED arrays.

In one arrangement, it was found convenient to use LED devices manufactured by Stanley known as ESBR diodes. The current flowing through the diodes is typically 20 to 30 milliamps and less than 50 milliamps. The zero adjust network 124 ensures that the LED devices are not reversed biased at any stage in the process because this would have the effect of upsetting the otherwise purely sinusoidal inputs to the LED devices.

Figure 9:
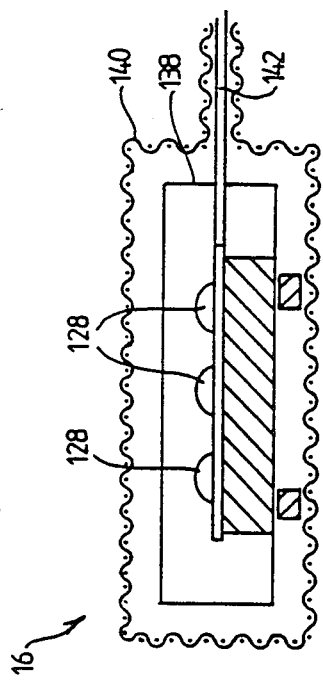
FIG. 9 is a schematic side view of the LED array with shielding.
Figure 8:
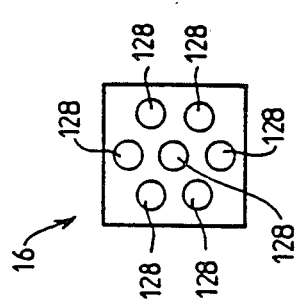
FIG. 8 is a schematic view of an LED array.

It has been found desirable to locate the LED arrays 16 within inner and outer shielding screens 138 and 140 as shown in FIG. 9. The screens substantially eliminate the effects of electric and magnetic fields produced by the currents flowing through the LED's 128. The conductors 142 to the array 16 are also shielded for the same reason. Shielding is very important from a practical point of view because of the proximity of the array 16 to the EEG electrodes and because of the relatively low signal level, i.e. signals at the selected frequencies $F_1$, $F_2$ and $F_3$ compared to the background EEG signal. Typically the signal level at the reference frequencies might be less than 2 microvolts whereas the background level could be 20 volts.

FIG. 10 illustrates in more detail the analyser circuit 18. It comprises an input amplifier 144 which receives an EEG signal from the electrodes 4, 6, 8 and 10. Output from the amplifier passes to a band pass filter 146 selected to pass frequencies say in the range 1 to 100 Hz. Output from the filter 146 is coupled to the inputs of multiplying digital to analogue converters 148, 150, 152, 154, 156 and 158. Other inputs to the converters are from the ROM's 58, 60 and 62 of the stimulus generator 14. The sine output lines 64, 66 and 68 are connected to the converters 148, 152 and 156 respectively. The cosine output lines 70, 72 and 74 are connected to the converters 150, 154 and 158 respectively. The output of the converters are coupled to the inputs of integrators 160, 162, 164, 166, 168 and 170, the outputs of which are coupled to sample and hold circuits 172, 174, 176, 178, 180 and 182 respectively. The integrators and sample and hold circuits are controlled by output signals from the ROM's of the generator 14. More particularly, the integrators 160 and 162 and sample and hold circuits 172 and 174 are controlled by the control lines 76 from the ROM 58 and are thus used for analysis at the reference frequency $F_1$. The integrators 164 and 166 and sample and hold circuits 176 and 178 receive control signals via the lines 78 from the ROM 60 and are used for reference frequency $F_2$. The integrators 168 and 170 and circuits 180 and 182 are controlled by signals on the control line 80 from ROM 62 and are used for reference frequency $F_3$. Outputs from the sample and hold circuits are coupled to an analogue to digital converting device 184 via a multiplexer 186 which in turn is controlled by the microcomputer 12 via line 187. The converting device 184 is controlled by the microcomputer 12 via control lines 189. Data output from the converter 184 is applied to the microcomputer 12 for further processing.

Generally speaking, the arrangement of FIG. 10 is used to enable very accurate selection from the EEG signal received by the amplifier 144 of components at the reference frequencies $F_1$, $F_2$ and $F_3$. Further, the discrimination can be performed in a relatively short time so that information is available to the computer 12 to allow updating of displayed information at a reasonable repetition rate.

Output signal of the filter 146 denoted f(t) will include components at the selected frequencies $F_1$, $F_2$ and $F_3$. Considering firstly the frequency $F_1$, the output signals from the converters 148 and 150 will be as follows:

output of converter 148 = $f(t) \cdot \text{Sin } 2\pi f_1$ output of converter 150 = $f(t) \cdot \text{Cos } 2\pi f_1$ because of the inputs from lines 64 and 70 from the ROM 58. The integrators 160 and 162 are arranged to integrate the outputs from the converters 148 and 150 for a selected number of full cycles of the at the selected frequency $F_1$ as determined by control lines 76. Thus the outputs of the integrators 160 and 162 are as follows:

$$\text{output of integrator 160} = \int_0^{2\pi} f(t) \cdot \text{Sin } 2\pi F_1 \cdot dt$$

$$\text{output of integrator 162} = \int_0^{2\pi} f(t) \cdot \text{Cos } 2\pi F_1 \cdot dt$$

By Fourier analysis it can be shown that the magnitude $M_1$ of the component of the EEG signal f(t) at frequency $F_1$ can be calculated as follows:

The output values of the integrators 160 and 162 at the end of each period of the frequency $F_1$ will be held in the sample and hold circuits 172 and 174 for conversion to digital from in the converter 184 and for transfer to the microcomputer 12 for averaging over the required number of cycles indicated in Table 1. The averaged outputs of circuits 172 and 174 are then squared, summed and the square root obtained to determine the value $M_1$. For instance at $F_1 = 4$ Hz, there are 80 cycles whereby the value of $M_1$ is averaged over these 80 cycles thus yielding a reasonably accurate result in a relatively short time.

The other selected frequencies $F_2$ and $F_3$ in the group are processed in a similar manner, the outputs of sample and hold circuits 176 and 178 being relevant to frequency $F_2$ and the outputs of sample and hold circuits 180 and 182 being relevant to frequency $F_3$.

The use of the multiplexer 186 under control of the microcomputer 12 enables a single analogue to digital converter 184 to be utilized. Thus the average values $M_1$, $M_2$ and $M_3$ of the frequency components at the frequencies $F_1$, $F_2$ and $F_3$ can be calculated and stored in the microprocessor 12. The stored information can then be transferred to the computer 20 and used to provide graphical output in the format as shown for instance in FIG. 3A or FIG. 3D.

If required, the phase change can also be computed for generating an output display of the type shown in FIG. 3B. The phase difference can be calculated using the following formula:

$$\Delta \phi = \pi/2[1 - \text{Sgn}(B_n)] + A\tan B_n/A_n$$

where
$\text{Sgn}(B_n) = +1 \quad\quad 0 \leq B_n$
$\text{Sgn}(B_n) = -1 \quad\quad B_n < 0$ and $A_n = \int_0^{N/f_1} f(t) \cdot \text{Sin } 2\pi F_1 \cdot dt$ $B_n = \int_0^{N/f_1} f(t) \cdot \text{Sin } 2\pi F_1 \cdot dt$ N = number of cycles at $F_1$ over which integration takes place It will be appreciated that the coefficients $A_n$ and $B_n$ are directly related to the outputs of the sample and hold circuits 172 and 174 and are therefore readily available for determination and subsequent processing.

Similarly, the phase response for the frequencies $F_2$ and $F_3$ can be obtained from the sample and hold circuits 176, 178 and 180, 182 respectively.

The circuit of FIG. 10 is particularly suitable in the arrangement of the invention because the analogue integrators 160-170 enable very rapid and accurate computation of the required integrals. The remaining mathematical processing is however most conveniently done in digital form in the computers 12 and 20, it being largely a matter of convenience where the computations are performed.

$$M_1 = \sqrt{\left[\int_0^{2\pi} f(t) \cdot \text{Sin } 2\pi F_1 \cdot dt\right]^2 + \left[\int_0^{2\pi} f(t) \cdot \text{Cos } 2\pi F_1 \cdot dt\right]^2}$$

Figure 11:
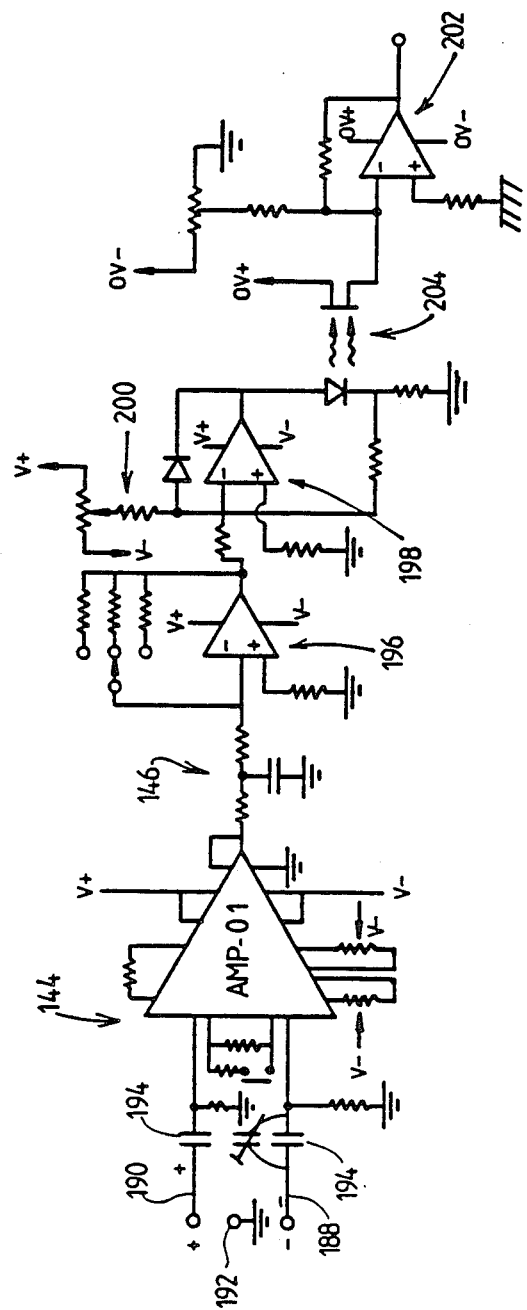
FIG. 11 is a circuit diagram of part of the analyser.

FIG. 11 illustrates in more detail the amplifier 144 and filter 146. The amplifier 144 comprises a precision instrumentation differential amplifier (AMP-01) the negative input 188 of which is connected to the electrodes 8 and 10 connected to the ear of the subject. The positive input 190 is connected to the electrode 6 at the central occipital site and the ground input 192 is connected to the electrode 4 at the forehead of the subject. The inputs 188 and 190 include coupling capacitors 194 to filter out very low frequency components say below 1 Hz and can thus be regarded as part of the filter 146. Output from the amplifier 144 passes to a resistance-capacitance network which comprises the remainder of the filter 146 and operates to attenuate frequencies above say 100 Hz. Output from the filter 146 is then amplified in a pair of amplifiers 196 and 198, the latter including a DC offset network 200 for adjustment of the DC output level of the amplifier 198. The output of the amplifier 198 is coupled to the input of a further amplifier 202 via an optocoupler 204. The optical coupling is particularly important because the amplifier 144 is directly coupled to the head of the subject via the EEG electrodes and for safety reasons it is important to use a battery for the power supply for the amplifiers 144, 196 and 198. The use of the optocoupler 204 ensures that these components are not electrically connected with the remainder of the circuit which can be powered from a mains supply. It follows that should there be any equipment malfunction, there is very little likelihood of excessively high voltages or currents being applied to the subject.

Figure 12:
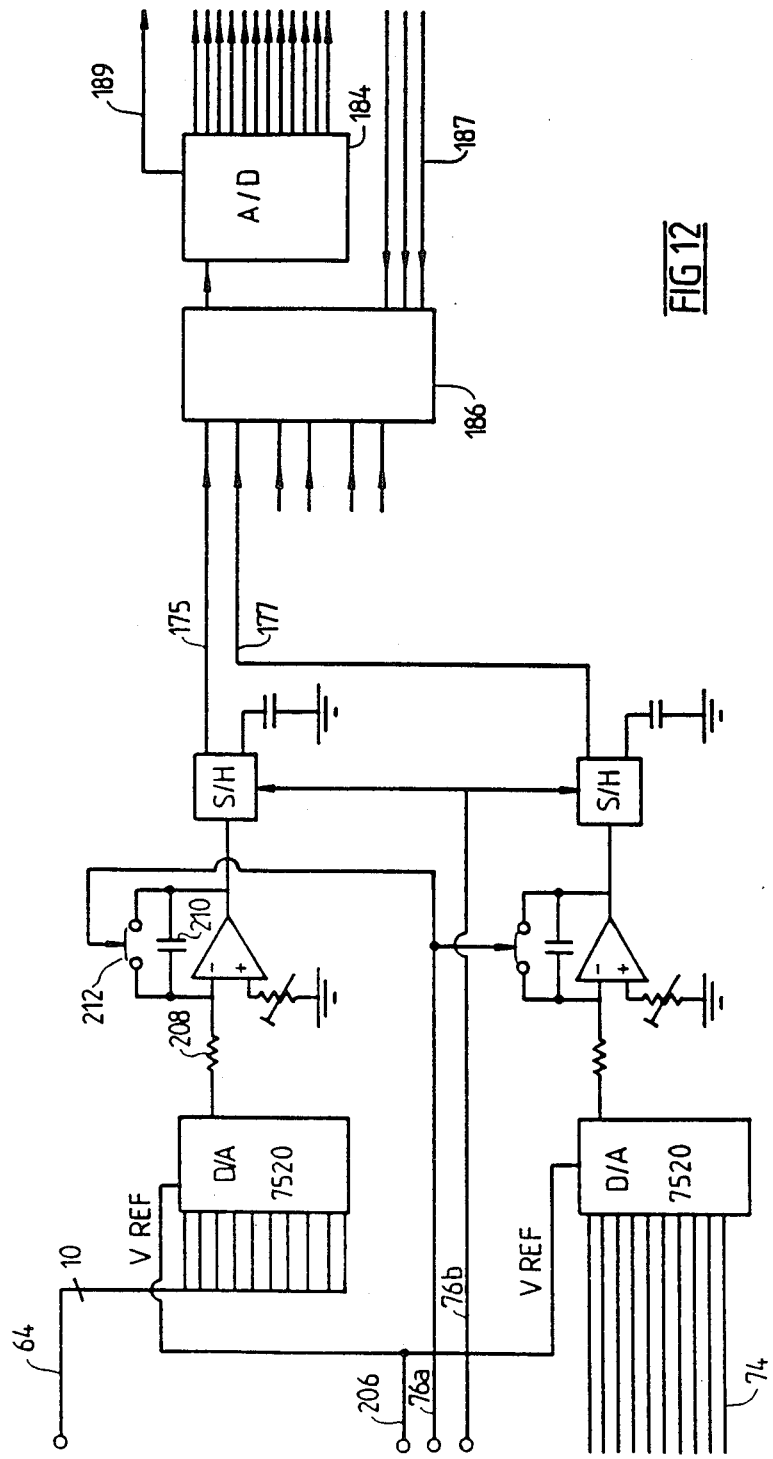
FIG. 12 is another circuit diagram of part of the analyser.
Figure 13:
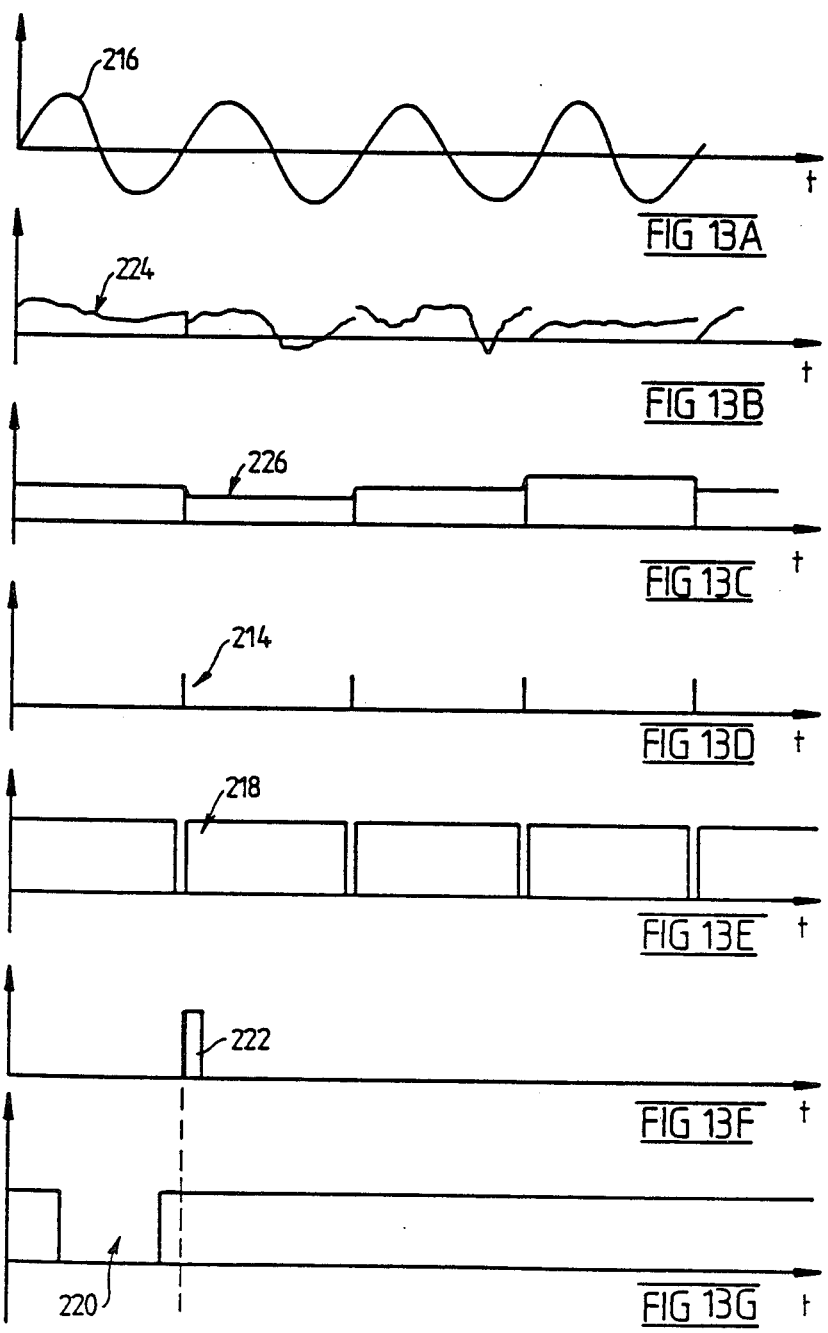
FIGS. 13A to 13G show waveforms useful in understanding the operation of the invention.

FIG. 12 shows in more detail a circuit realization for the arrangement shown in FIG. 10. Output from the amplifier 202 is applied to input line 206 which is connected to the reference inputs of the multiplying digital to analogue converters 148 and 140 which may comprise type 7520 circuits. The converter 148 receives the sine signal on lines 64 from the ROM 58 whereas the converter 150 receives the cosine signal on lines 74 from the same ROM. The converters 148 and 150 thus produce products in analogue form proportional to the EEG signal multiplied by the sine and cosine functions at reference frequency $F_1$. The output from the converter 148 passes to the input of the integrator 160 which comprises a TL 072 amplifier having an input resistor 208 and feedback capacitor 210 so that the amplifier functions as an analogue integrator in the usual way. The capacitor 210 is bridged by an analogue switch 212, which is of type 4066, and receives control signals on control line 76a from the ROM 58. The waveform of the control signal on the line 76a is represented by waveform 214 in FIG. 13D. The waveform 214 closes the switch 212 which results in rapid discharging of the capacitor 210 at or just after the zero crossings of the reference frequency $F_1$ which is represented by waveform 216 in FIG. 13A. The sample and hold circuit 172 is controlled to hold the value of the integrator just prior to its being discharged on closing of the switch 212. This is effected by control signals on control line 76b which have the waveform 218, as shown in FIG. 13E. FIGS. 13F and 13G show the sequence of the control signals on lines 76a and 76b respectively on an expanded time scale. It will be seen that the negative going pulse 220 which actuates the sample and hold circuit 172 occurs prior to the positive going pulse 222 which causes closure of the switch 212. When the sample and hold circuit 172 receives the leading edge of the pulse 220 it causes the circuit 172 to track the output of the integrator and the trailing edge triggers the start of the holding cycle. FIG. 13B illustrates a typical output waveform 224 of the integrator 160 and FIG. 13C shows a typical output waveform 226 of the sample and hold circuit 172. It will be observed in the waveform 226 that the tracking period occurs just prior to the zero crossings of the reference frequency $F_1$. Thus, the output waveform 226 of the circuit 172 during each cycle of the reference frequency $F_1$ represents the value of the integral at the output of the integrator 160 at the end of each cycle. An analogous waveform is obtained at the output of the sample and hold circuit 174 for the cosine product integral. The outputs from the circuits 172 and 174 are connected to the multiplexer 186 via lines 175 and 177 for processing as described previously. Similar circuitry is also provided for the reference frequencies $F_2$ and $F_3$ so as to enable simultaneous processing of three reference frequencies.

Figure 14:
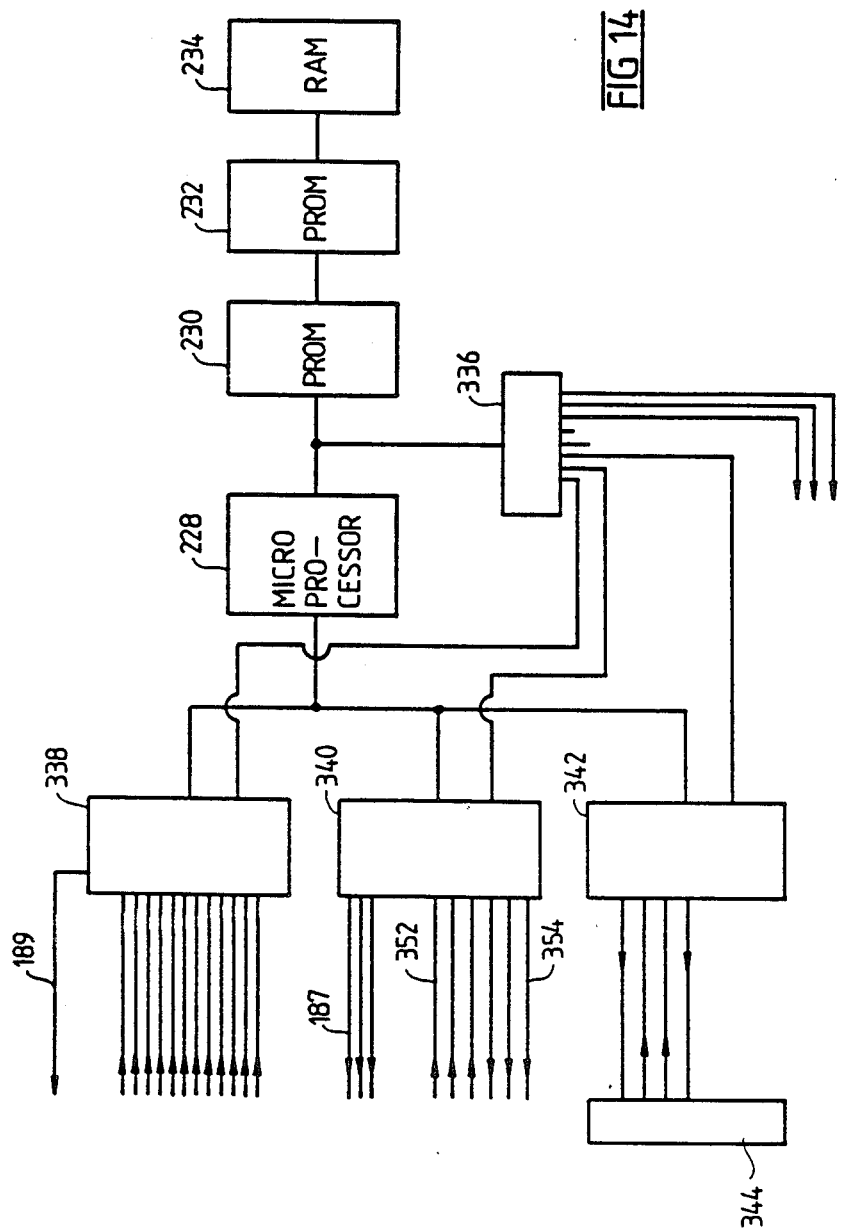
FIG. 14 is a block diagram of a microprocessor used in the system.

FIG. 14 illustrates schematically one configuration for the microcomputer 12. It comprises a 6082 series CPU 228, two 2732 PROM's 230 and 232, and a 6116 RAM 234. The circuit includes a selector 336 for providing address decode information for the frequency multipliers 40, 42 and 44 i.e. data for the latch 104 shown in FIG. 5 in relation to reference frequency $F_1$. The circuit includes three input/output units 338, 340 and 342 for providing communication with the components in the stimulus generator 14 and analyser 18. The circuit includes an RS 232 interface connector 344 for coupling to the general purpose microcomputer 20.

Figure 15:
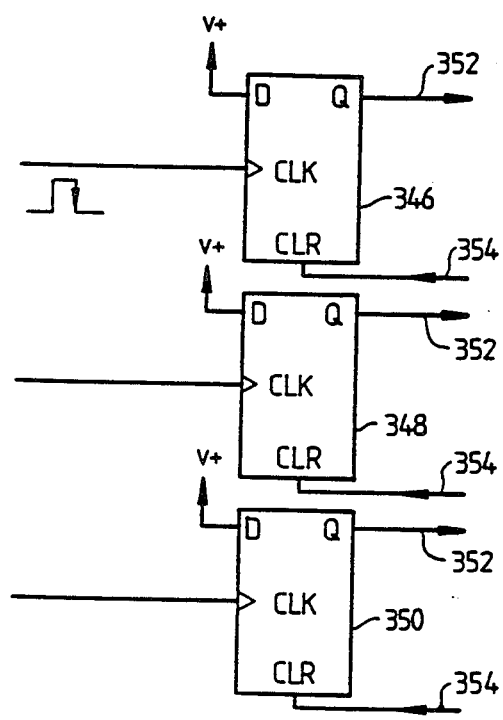
FIG. 15 is a schematic diagram of components associated with the microprocessor.

FIG. 15 shows in diagrammatic form three flip flops 346, 348 and 350 used to flag various service requests required for the operation of the stimulus generator 14 and analyser 18. The outputs of the flip flops are inputted to the input/output unit 340 via lines 352 and 354, as seen in FIG. 14.

The principles of the invention disclosed herein are applicable to other sensory organs such as the ears of a subject so as to enable assessment of consciousness of the subject.

Many modifications will be apparent to those skilled in the art without departing from the spirit and scope of the invention.

I claim:

1. A method of testing anaesthetic depth or consciousness of a subject (2) having closed eyelids, comprising the steps of applying a stimulus signal (216) of visible red light, whose intensity is varied so as to include at least one component of a predetermined frequency ($F_1$, $F_2$, $F_3$), to at leat one closed eyelid of the subject, said stimulus signal (216) being perceptible to the subject (2) through said closed eyelid, obtaining an electroencephalographic (EEG) signal from the subject while said stimulus signal is being applied and perceived by the subject (2), analysing the EEG signal so as to determine the magnitude, or magnitude and phase of that component of the EEG signal which has said predetermined frequency, and assessing the anaesthetic depth or consciousness of the subject with reference to said magnitude, or magnitude and phase of the component.

2. A method as claimed in any one of claim 1 including the step of applying a stimulus signal having a plurality of predetermined frequency components therein and the analysis of the EEG signal is carried out to determine the magnitude, or magnitude and phase of the respective components in the EEG having the same frequencies as the stimulus signal.

3. A method as claimed in any one of claim 1 including the step of simultaneously applying selected groups of said frequency components.

4. A method of testing anaesthetic depth or consciousness of a subject (2) comprising the steps of applying a stimulus signal (216) having a plurality of predetermined frequency components simultaneously therein, to a sensory organ of the subject, obtaining an electroencephalographic (EEG) signal from the subject while said stimulus is being applied, analysing the EEG signal so as to determine the magnitude, or magnitude and phase of the respective components of the EEG signal which have the same frequencies as said plurality of predetermined frequency components, and assessing the anaesthetic depth or consciousness of the subject with reference to said magnitude, or magnitude and phase of the respective components.

5. A method as claimed in claim 4 wherein said plurality of frequency components have frequencies selected from the range 38 to 72 Hz.

6. A method as claimed in claim 4, including the step of obtaining a normal response (22, 32) for the subject by obtaining a normal electroencephalographic (EEG) signal from the subject prior to administering anaesthetic to the subject, and wherein said step of assessing the anaesthetic depth or consciousness includes the step of comparing the first mentioned EEG signal with said normal EEG signal.

7. A method as claimed in claim 6 including the step of graphically displaying said EEG signals or a ratio thereof.

8. A method as claimed in claim 6 wherein said stimulus signal comprises electromagnetic radiation.

9. A method as claimed in claim 8 wherein the radiation comprises visible red radiation modulated in intensity so as to have components as said plurality of predetermined frequencies.

10. A method as claimed in claim 9 wherein the predetermined frequencies are in the range from 4 to 72 Hz.

11. A method as claimed in claim 4 wherein the EEG signal from the subject is separately multiplied by the sine and cosine of each frequency component $f_n$ of the stimulus signal and then integrated as a function of time, and the magnitude $M_n$ of the EEG signal at frequency $f_n$ is determined by performing the following calculation:

$$M_n = \sqrt{\left[\int_0^{2\pi} EEG \cdot \operatorname{Sin}2\pi f_n \cdot dt\right]^2 + \left[\int_0^{2\pi} EEG \cdot \operatorname{Cos}2\pi f_n \cdot dt\right]^2}$$

12. A method as claimed in claim 34 wherein the steps of multiplying by the sine and cosine of each frequency and the integration are performed in analogue form.

13. A method as claimed in claim 4 including the step of administering anaesthetic to the subject in accordance with the assessment of anaesthetic depth.

14. Apparatus for testing consciousness of a subject having closed eyelids, said apparatus comprising generator means (14) for generating a stimulus signal of visible red light, whose intensity is varied so as to have at least one component of a predetermined frequency, coupling means (16) for coupling the stimulus signal to at least one closed eyelid of the subject, said stimulus signal being perceptible to the subject through said closed eyelid, EEG electrodes (4, 6, 8, 10) for deriving an EEG signal from the subject and discriminating means (18) for obtaining magnitude, or magnitude and phase of that component of the EEG signal which has said predetermined frequency.

15. Apparatus as claimed in claim 14 wherein the coupling means comprises an LED array (16) for applying intensity modulated infra red signals to the eye or eyes of the subject through his closed eyelid or eyelids.

16. Apparatus as claimed in claim 15 wherein the generator means includes an intensity control circuit (90) which regulates the peak intensity of light emitted from the LED array, said intensity control circuit including a control LED (132) output from which provides negative feedback for controlling driving current to the LED array.

17. Apparatus as claimed in claim 15 wherein the LED array is coupled to the intensity control circuit via an optocoupler.

18. Apparatus as claimed in claim 17 wherein the LED array is located within a shielding screen (138, 140).

19. Apparatus as claimed in claim 15 wherein the LED array is in two portions which overlie in use respective eyes of the subject.

20. Apparatus as claimed in claim 19 wherein said portions are mounted on goggles or a spectacle frame.

21. Apparatus as claimed in claim 14 wherein the generator means generates a plurality of predetermined frequency components ($F_1$, $F_2$, $F_3$) which are, in use, simultaneously applied to the subject and the discriminating means determines the magnitude, or magnitude and phase of the respective components of the EEG signal.

22. Apparatus for testing consciousness of a subject, said apparatus comprising generator means (14) for generating a stimulus signal having a plurality of predetermined frequency components simultaneously therein, coupling means (16) for coupling the stimulus signal to a sensory organ of the subject, EEG electrodes (4, 6, 8, 10) for deriving an EEG signal from the subject and discriminating means (18) for obtaining the magnitude, or magnitude and phase of the respective components of the EEG signal which have the same frequencies as said plurality of predetermined frequency components.

23. Apparatus as claimed in claim 22 wherein said plurality of frequency components have frequencies selected from the range 38 to 72 Hz.

24. Apparatus as claimed in claim 22 wherein the discriminating means includes a plurality of multiplier circuits (148-158) for separately multiplying the EEG signal by the sine and cosine of each frequency component $f_n$ of the stimulus signal, and a plurality of integrator circuits (160-170) for integrating the outputs of the multiplier circuits.

25. Apparatus as claimed in claim 24 wherein the outputs of the integrator circuits are coupled to inputs of respective sample and hold circuits (172-182) which hold the output values of the integrator circuits at the end of each period of the frequency component $f_n$ of the stimulus signal.

26. Apparatus as claimed in claim 25 wherein the outputs of the sample and hold circuits are averaged over a preselected number of cycles to obtain average values of sine and cosine integrals at each frequency component and wherein the discriminating means includes an arithmetic unit (12) for calculating the magnitude $M_n$ of the EEG signal at frequency $f_n$ by taking the square root of the sum of the squares of the respective average values at each frequency component $f_n$.

27. Apparatus as claimed in claim 26 including a multiplexer (186) and an analogue to digital converter (184) and wherein the outputs of the sample and hold circuits are coupled to the converter via the multiplexer and wherein said arithmetic unit performs its operations in digital form.

* * * * *

UNITED STATES PATENT AND TRADEMARK OFFICE
CERTIFICATE OF CORRECTION

PATENT NO. : 4,869,264
DATED : September 26, 1989
INVENTOR(S) : Silberstein

It is certified that error appears in the above—identified patent and that said Letters Patent is hereby corrected as shown below:

Col. 1, line 64 - Change "signalf rom" to -- signal from --.

Col. 2, line 53 - Change "and" (second instance) to -- are --.

Col. 3, line 54 - Change "In" to -- If --.

Col. 4, line 19 - Delete "is" (first instance).

Col. 7, line 47 - Delete "of the".

Col. 8, line 31 - Change "Bn/An" to -- An/Bn --.

Col. 11, line 36 - Change "as" to -- at --. (2nd occurrence)

Signed and Sealed this

Second Day of October, 1990

Attest:

HARRY F. MANBECK, JR.

*Attesting Officer*      *Commissioner of Patents and Trademarks*